United States Patent [19]

Engler et al.

[11] 4,028,346

[45] June 7, 1977

[54] TETRASELENOFULVALENE, DITHIODISELENOFULVALENE AND THE TCNQ SALTS THEREOF

[75] Inventors: Edward M. Engler, Wappingers Falls; Vishnubhai V. Patel, Ossining, both of N.Y.

[73] Assignee: International Business Machines Corporation, Armonk, N.Y.

[22] Filed: June 10, 1974

[21] Appl. No.: 477,553

[52] U.S. Cl. .................... 260/239 R; 260/327 M; 260/327 R

[51] Int. Cl.² .................................. C07D 421/04

[58] Field of Search ....... 260/239 R, 327 R, 327 M

[56] References Cited

OTHER PUBLICATIONS

Corey et al., "Tetrahedron Letters" vol. 33, pp. 3201–3204 (1967).
Ferraris et al., J. Am. Chem. Soc., vol. 95, pp. 948 and 949 (1973).
Wudl et al., J. Am. Chem. Soc., vol. 94, pp. 670 and 671 (1972).
Corey et al., JACS, vol. 87, 1965, pp. 934 and 935.
Hartzler JACS, vol. 95, 1973, pp. 4379 and 4385.
Bechgaard et al. "J.C.S. Chem. Comm.", 1974, pp. 937 and 938.
Wudl et al. J.C.S. Chem. Comm. 1970, pp. 1453 and 1454.
Challenger et al., J. Chem. Soc. (1953). pp. 292–304.
Goodings, "Endeavour," 34, pp. 123–130 (1975).
Hunig et al., "Liebings Ann. Chem.," (1973), pp. 310–323.
Jensen Quarterly Reports on Sulfur Chem., vol. 5, No. 1, pp. 45–52 (1970).

Primary Examiner—Raymond V. Rush
Assistant Examiner—D. B. Springer
Attorney, Agent, or Firm—Hansel L. McGee; Alvin J. Riddles

[57] ABSTRACT

Organic molecules can be coupled via their selenocarbonyl derivatives. Generally, the synthesis can be described by the following reaction equation:

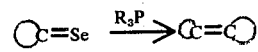

where ⊂C can be a cyclic or heterocyclic organic compound and R can be alkoxy, phenoxy or phenyl, preferably $CH_3O$, $C_2H_5O$, $C_6H_5O$, $C_6H_5$ and the like. The reaction is usually carried out in a refluxing solvent, the choice of the solvent being determined by the stability and by the ease of coupling of a particular substrate. Groups that tend to stabilize the selenocarbonyl require higher boiling solvents and longer refluxing times. Aromatic solvents, such as benzene or toluene are well-suited for the coupling reaction. In some cases, refluxing the substrate in the alkoxy-phosphorus base as solvent may be advantageous. This new coupling procedure permits the synthesis of the hitherto unknown compounds: tetraselenofulvalene (TSeF), the selenium analogue of tetrathiofulvalene (TTF), and diselenodithiofulvalene (DSeDTF). Highly conducting charge transfer salts of tetraselenofulvalene and diselenodithiofulvalene with tetracyano-p-quinodimethane have also been prepared. The materials of this invention are useful in the organic electronic devices described in copending application Ser. no. 450,541 to Arieh Aviram et al. and assigned to the same assignee as is the present application.

4 Claims, No Drawings

ND THE TCNQ
TETRASELENOFULVALENE, DITHIODISELENOFULVALENE AND THE TCNQ SALTS THEREOF

BACKGROUND OF THE INVENTION

This invention relates to a general method for the coupling of ring systems with easily oxidizable heteroatoms. More particularly, it relates to a novel method for synthesizing seleniumfulvalene derivatives by deselenization with alkoxy phosphorous bases of selenocarbonyls. It also relates to the preparation of the tetracyano-p-quinodimethane charge transfer salts of tetraselenofulvalene (TSeF) and diselenodithiofulvalene (DSeDTF) and their derivatives.

Considerable interest has been shown recently in the study of highly conducting organic charge transfer salts. The most attractive of these systems is the salt between tetrathiofulvalene (TTF) and tetracyano-p-quinodimethane (TCNQ) which displays exceptional electrical conductivity and metallic behavior over a wide temperature range. Further, a few anomalous crystals of TTF-TCNQ have been reported by L. B. Coleman et al, Solid State Commun. 12, 1125 (1973) to exhibit "giant" conductivity maxima. Attempts have been made to enhance the metallic properties of the tetrathiofulvalenium radical cation by substitution of electron-releasing substituents. Such substitution also results in considerable distortion of the TTF-TCNQ crystal structure. In order to improve upon the metallic properties of fulvalenium systems in a definable and controllable way, there has been devised a synthesis of tetraselenofulvalene (TSeF) and its charge transfer salt with TCNQ. The larger, more polarizable selenium reduces coulombic repulsion and increases electronic interaction, possibly by enhanced overlap of the cation radicals. Furthermore, this modification has essentially kept constant the original TTF-TCNQ crystal structure.

It has been found that the hitherto unknown tetraselenofulvalene (TSeF) cannot be synthesized in the same manner as its analogue, tetrathiofulvalene (TTF). The basic reactions used for TTF are shown in the publications to F. Wudl et al., Chem. Commun. 1453 (1970) and D. L. Coffen, et al., J. Amer. Chem. Soc., 93, 2258 (1971). The synthesis involves the oxidation of vinylene trithiocarbonate (1) followed by base coupling. The reaction sequence is outlined below in equation 1:

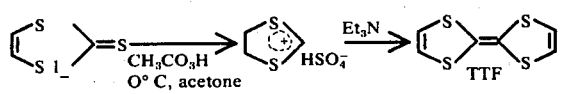

The oxidation step in the above reaction sequence fails when easily oxidizable heteroatoms such as selenium are used in place of sulfur in compound 1.

Accordingly, it is an important aspect of this invention to provide a method for coupling ring systems having easily oxidizable heteroatoms in the ring system. It is a further object to provide a method for producing tetraselenofulvalene and related systems. It is yet another object to provide charge transfer salts prepared from TSeF and related systems with TCNQ.

SUMMARY OF THE INVENTION

In accordance with the invention, there is provided a novel method for coupling ring compounds having the selenocarbonyl bond (C=Se). The ring compound can be selected from any cyclic organic compound and may be saturated, unsaturated or heterocyclic. The method comprises the step of treating the cycloselenocarbonyl compound with an alkyl phosphorous base in a refluxing organic solvent. Illustrative of this novel method, it is shown for the synthesis of tetraselenofulvalene and its derivatives. The general reaction is as follows:

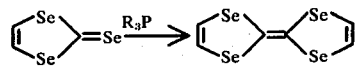

Synthetic procedures are well-known for converting carbonyl or thiocarbonyl compounds to selenocarbonyl compounds. Some examples of these procedures are reported in the publications to G. Traverso, Ann. Chim. (Rome) 47, 3, 1244 (1957) and H. E. Hallam and C. M. Jones, J. Chem. Soc., B, 1033 (1969).

The foregoing and other objects, features and advantages of the invention will be apparent from the following more particular description of preferred embodiments of the invention.

DESCRIPTION OF PREFERRED EMBODIMENTS

Because considerable interest has recently been shown for highly conducting organic charge transfer salts, this invention will be illustrated by the preparation of tetraselenofulvalene, the selenium analogue of tetrathiofulvalene. As noted above, the most attractive of the organic charge transfer salt systems is that between tetrathiofulvalene and tetracyano-p-quinodimethane which displays high electrical conductivity ($\delta_{max}58°Kca10^4(ohm-cm)^{-1}$) and metallic behavior over a wide temperature range, as discussed in the publications to J. Ferraris, et al., J. Amer. Chem. Soc. 95, 948 (1973) and to L. B. Coleman, et al., Solid State Communications, 12, 1125 (1973). It is believed that the electrical conductivity and the metallic behavior of this system can further be enhanced by the substitution of selenium for sulfur in tetrathiofulvalene since the larger more polarizable selenium tends to reduce coulombic repulsions and increase electronic interactions because of enhanced overlap between the donor molecules in these charge transfer salts. Furthermore, this modification has essentially kept constant the steric requirements of the original TTF-TCNQ crystal structure.

The coupling of vinylene triselenocarbonate to give tetraselenofulvalene (TseF) was not obtainable using known reaction schemes. For example, Wudl, et al, Chem. commun. 1453 (1970) and D. L. Coffen et al, J. Amer. Chem. Soc. 93:9 (1971) coupled vinylene trithiocarbonate by oxidation with a peracid, followed by treatment with a base. This method, however, when applied for the preparation of the selenium analogue of TTF, did not yield the desired compound.

The reaction scheme of the present invention can generally be given as follows:

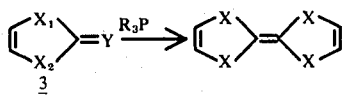

where X can be selected from the group consisting of S, Se, Te and other heteroatoms, and $X_1$ and $X_2$ can either be the same or different atoms; Y is Se. It should be noted that while the invention will generally be described showing the syntheses of TSeF, DSeDTF and TTF, other ring compounds can be coupled according to the above reaction scheme. The preparation of compounds such as 3 in the above scheme are known in the art, and the details therefor can be found in the publication to Mayer and Gebhardt, Chem. Ber., 97, 1298 (1964). It should also be noted that when Y is S, the above reaction does not yield the desired coupled product. This further points up the deviation between sulfur and selenium chemistry.

EXAMPLES

The method of coupling organic compounds according to the invention will now be described by way of example.

Selenium derivatives of vinylene trithiocarbonate used are prepared by an extension of the method of Mayer et al. and given by the equations shown below. For example, the diselenothiocarbonate (4) was prepared according to the scheme:

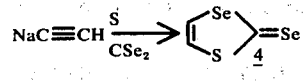

The dithioselenocarbonate (5) was prepared as follows:

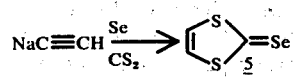

The triselenocarbonate (2) was prepared as follows:

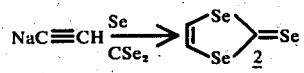

The tellurium analogues may be prepared in a similar manner except that Te is substituted for Se.

EXAMPLE 1

Synthesis of Tetraselenofulvalene (TSeF)

A two molar excess of trimethylphosphite is added to a benzene solution containing vinylene triselenocarbonate (2) under $N_2$. The reaction mixture is refluxed and the reaction is complete in about 5 hours. The benzene is removed on a rotary evaporator. The residue is then extracted with hot hexane. Upon cooling, orange red needles of tetraselenofulvalene are precipitated. The crystals have a m.p. of 132°–133° C. Analysis of the product showed: nmr ($CHCl_3$, δrel. to TMS): 7.25; uv-vis. [hexane, λmax (log ε)]: 490 (2.18), 365(3.08), 300(4.00), 289(4.07); m/e: 396(based on $^{80}Se$).

EXAMPLE 2

Synthesis of Tetrathiofulvalene

Tetrathiofulvalene is prepared in the same manner as in Example 1 except that a benzene solution containing dithioselenocarbonate is used. Analysis of the product was favorably compared with that of published value of Wudl et al., Chem. Commun., 1453 (1970). The orange crystals of TTF had a m.p. of 119°–120° C; nmr ($CDCl_3$ δ rel. to TMS): 6.33; uv-vis. [hexane, λ max. (log ε)]: 455 (2.48), 360 (3.23), 316 (4.06), 303 (4.12); m/e: 204.

EXAMPLE 3

Synthesis of Dithiodiselenofulvalene

Dithiodiselenofulvalene is prepared in the same manner as in Example 1 except that a benzene solution containing thiodiselenocarbonate is used. The product was orange crystals which had an analysis as follows: m.p. 115°–116° C.; nmr ($CDCl_3$ δrel. to TMS): 7.1, 6.5 (AB pattern, $J_{AB} = 7Hz$); mass spectrum: molecular ion, 300 (based on $^{80}Se$).

EXAMPLE 4

Synthesis of TSeF-TCNQ Salt

The salt of TSeF-TCNQ is prepared by mixing equal molar amounts of TSeF and TCNQ in acetonitrile. Crystals of TSeF-TCNQ are grown by diffusing the acetonitrile mixture in a U-tube. A 1:1 complex is formed having an elemental analysis as follows based on the formula $C_8H_8N_4Se_4$:

Calc'd C, 36.25; H, 1.35; N, 9.40; Se, 53.00
Found C, 36.28; H, 1.25; N, 9.24; Se, 53.23. TSeF-TCNQ is one of the highest conducting organic compounds presently known and exhibits metallic behavior to a lower temperature (40° K as compared to 58° K for the TTF analog) than any other known organic material. The d.c. electrical conductivity of TSeF-TCNQ at 40° K is found to be approximately $10^4 (ohm-cm)^{-1}$.

EXAMPLE 5

Synthesis of DSeDTF-TCNQ Salt

The salt of DSeDTF-TCNQ is prepared in the same manner as in Example 4. It is found to be highly conducting at a comparatively low temperature (67° K). Its d.c. conductivity at 67° K is approximately $5 \times 10^3 (ohm-cm)^{-1}$.

Attempts were made to prepare the selenium adducts of tetrathiofulvalene according to the method described in the publication to Wudl et al., Chem. Commun. 1435 (1970).

EXAMPLE 6

A threefold excess of 50% peracetic acid is added dropwise to an acetone solution of vinylene diselenothiocarbonate at 0° C with stirring. A red solid precipitated from the reaction mixture. The precipitate is filtered and washed with cold acetone. The product is found to be insoluble in water, acetonitrile and chloroform. Its insolubility in water indicated that the desired oxidation product (tetraselenofulvalene) was not formed. Subsequent treatment of the product with a two molar excess of triethylamine in acetonitrile did not yield diselenodithiofulvalene.

EXAMPLE 7

The method of Example 6 was repeated except that an acetone solution of triselenocarbonate is used. The product was treated in the same manner and was found not to be tetraselenofulvalene, the desired product.

There has been shown and described a novel method for coupling ring compounds having a selenocarbonyl bond. Similarly, there has also been shown a novel method for preparing compositions of matter.

The invention has been described in detail with particular reference to certain preferred embodiments thereof, but it will be understood that variations and modifications can be effected within the spirit and scope of the invention.

What is claimed is:

1. A composition of matter tetraselenofulvalene.
2. A composition of matter dithiodiselenofulvalene.
3. A composition of matter tetraselenofulvalenium tetracyano-p-quinodimethanide.
4. A composition of matter dithiodiselenafulvalene tetracyano-p-quinodimethanide.

* * * * *